United States Patent [19]

Bisch et al.

[11] Patent Number: 5,282,858
[45] Date of Patent: Feb. 1, 1994

[54] HERMETICALLY SEALED IMPLANTABLE TRANSDUCER

[75] Inventors: Michael E. Bisch; Shafiq A. Khuhro, both of St. Louis, Mo.; Paul DiCarlo, East Falmouth, Mass.

[73] Assignee: American Cyanamid Company, Me.

[21] Appl. No.: 716,584

[22] Filed: Jun. 17, 1991

[51] Int. Cl.⁵ .......................... A61F 2/18; A61N 1/00; H04R 25/00
[52] U.S. Cl. ...................... 623/10; 600/25; 381/162; 607/57
[58] Field of Search .................. 600/25; 623/10; 128/642, 784, 789, 420.5, 420.6; 381/68.3, 68.6, 154, 162

[56] References Cited

U.S. PATENT DOCUMENTS

| | | | |
|---|---|---|---|
| 2,402,392 | 6/1946 | Goldschmidt | 600/25 |
| 3,209,082 | 9/1965 | McCarrell et al. | 381/68.6 |
| 3,602,654 | 8/1971 | Victoreen | 181/130 X |
| 4,052,754 | 10/1977 | Homsy | 600/25 X |
| 4,481,950 | 11/1984 | Duggan | 128/419 PT |
| 4,547,631 | 10/1985 | Nieuwendijk et al. | 381/162 X |
| 4,706,689 | 11/1987 | Man | 128/903 |
| 4,762,135 | 8/1988 | van der Puije et al. | 128/784 |
| 4,957,478 | 9/1990 | Maniglia | 600/25 |
| 4,988,333 | 1/1991 | Engebretson et al. | 600/25 |
| 5,015,224 | 5/1991 | Maniglia | 600/25 |
| 5,085,628 | 2/1992 | Engebretson et al. | 600/25 |

FOREIGN PATENT DOCUMENTS

| | | | |
|---|---|---|---|
| 0242038 | 10/1987 | European Pat. Off. | H04R 25/02 |
| 3940632C1 | 6/1990 | Fed. Rep. of Germany | H04R 25/02 |
| 3918086C1 | 9/1990 | Fed. Rep. of Germany | H04R 25/02 |

Primary Examiner—Randall L. Green
Assistant Examiner—Elizabeth M. Burke
Attorney, Agent, or Firm—Brian R. Woodworth

[57] ABSTRACT

A hermetically sealed acoustic mechanism for an implantable hearing aid system having a signal processing unit having at least one electromechanical transducer coupled to the auditory system of a human. The transducer having an outer casing and at least one moving member extending outside the casing. The invention comprising a hermetically sealed bellows member having two ends and a generally cylindrical side wall. One end of the bellows member being hermetically affixed to the transducer casing and the other end of the bellows member being hermetically affixed to the moving member at a point outside the transducer casing. The side wall having a plurality of corrugations formed therein to allow the moving member to vibrate independently from the transducer casing while providing a hermetic seal protecting the interior of the transducer.

14 Claims, 3 Drawing Sheets

HERMETICALLY SEALED IMPLANTABLE TRANSDUCER

BACKGROUND OF THE INVENTION

The present invention relates generally to implantable hearing aids and, more particularly, to an implantable hearing aid having one or more hermetically sealed transducers for direct coupling to the middle ear. The electroacoustic transducers of the present invention may be either a microphone or a hearing aid receiver within the implantable hearing aid of the present invention.

The implantable hearing aid is intended to help a specific class of patients for which conventional hearing aids are inadequate. These patients have severe hearing impairments and require excessive amplification. Conventional means are limited by acoustic feedback and sound distortion. Patients have reported an increased clarity of sound and were able to identify speech equal to or better than that reported with conventional aids by using amplified sound directly coupled to the middle ear bones.

An implantable hearing aid of the type discussed herein is described in U.S. Pat. No. 4,988,333 issued Jan. 29, 1991, and in a related continuation-in-part Application Ser. No. 420,292, filed Oct. 12, 1989, both of which are incorporated herein by reference. An important requirement of an implantable hearing aid is for its components to be hermetically sealed so that the environment existing inside the middle ear cavity does not corrode and/or destroy the internal parts of the hearing aid device. In the embodiment of the prior art, a transducer is acoustically connected to an acoustical coupler. The acoustical coupler has a compliant synthetic rubber diaphragm or membrane is stretched across one end of the coupler which, when the coupler is used as a microphone, may be physically attached to the handle of the malleus by a wire hook, or it may be positioned to acoustically couple with the tympanic membrane. When the coupler is to be used as a transmitter or vibrator, the diaphragm can be physically attached to the stapes or other middle ear bone via an intermediate porous ceramic wafer which is glued to the diaphragm.

However, while the synthetic rubber membranes are easily vibrated for the transmission of sound waves, it may be difficult to actually obtain the necessary hermetic seal between the diaphragm and body of the acoustic coupler. The diaphragms of the prior art devices are typically manufactured from a porous synthetic rubber material which does not provide a proper hermetic seal to adequately protect the interior of the acoustical couplers. It would be desirable to have the diaphragm manufactured from a metal or non-porous material; however, it is important that the diaphragm not lose any of its compliancy so as to be able to properly transmit the acoustical pulsations or vibrations through the acoustic coupler.

In a second embodiment of the prior art acoustical couplers, a tube having a movable piston is disclosed which is mechanically coupled either between the malleus or tympanic membrane and the transducer or between the transducer and one of the middle ear bones. However, no structure is disclosed in the prior art for providing such a hermetically sealed acoustic coupler.

Accordingly, one of the objects of the present invention is to provide a transducer for use inside the middle ear cavity having a totally hermetically sealed container without compromising the function of the transducer and acoustic coupler of the prior art devices.

It is another object to provide a hermetically sealed means for use with existing transducers to provide an implanted middle ear assistance device capable of use without significant modification of the existing transducers.

SUMMARY OF THE INVENTION

The present invention provides a transducer having a hermetically sealed bellows member for direct insertion into the middle ear cavity. The transducer is sized to fit within the middle ear cavity without significant surgical alteration of the cavity. It can be used as a microphone for coupling with the malleus, the tympanic membrane or the external ear canal. The transducer may also be used as a receiver to act as a vibrator for causing mechanical vibration of one of the middle ear bones.

The transducer, in one embodiment, comprises an outer tubing member having a bellows member soldered or otherwise attached to the end of the outer tubing member. The bellows member is likewise soldered or otherwise permanently affixed to an inner rod or pin extending axially within the outer tubing member and extending from the transducer body outwardly through the center of the bellows member. The ends of the bellows member may be manufactured with flanges thereon or provided with other features to provide soldering surfaces for connection to the outer tubing means and inner rod or tube, respectively.

The side wall of the cylindrical portion of the bellows member having a plurality of generally "U" shaped corrugations provided therein to allow the inner rod extending outwardly from the transducer to vibrate axially relative to the outer cylindrical tubing in response to internal or external mechanical or acoustical vibrations depending on the end use of the transducer (i.e. transducer is connected as a microphone or receiver as discussed above). The material of the bellows member is preferably gold plated nickel or other biocompatible metals which are non-porous and of sufficient strength and flexibility to allow the bellows member to be made small and strong enough for use in the middle ear cavity and still retain the necessary flexibility to allow the inner rod or tube to transfer the mechanical or acoustical vibrations to or from the transducer as the case may be. The outer end of the inner rod or tube of the transducer may be physically coupled to the handle of the malleus by a wire hook or it may be positioned to couple with the tympanic membrane or membrane of the external ear cavity when used as a microphone. When the transducer is to be used as a receiver or vibrator, the outer end of the inner rod or tube of the transducer can be physically attached to or abutted against one of the middle ear bones to transmit the vibrations to the cochlea.

BRIEF DESCRIPTION OF THE DRAWINGS

The invention will become more apparent from the following detailed description, taken in conjunction with the appended drawings, in which.

DETAILED DESCRIPTION OF THE PREFERRED EMBODIMENT

Figure 3:
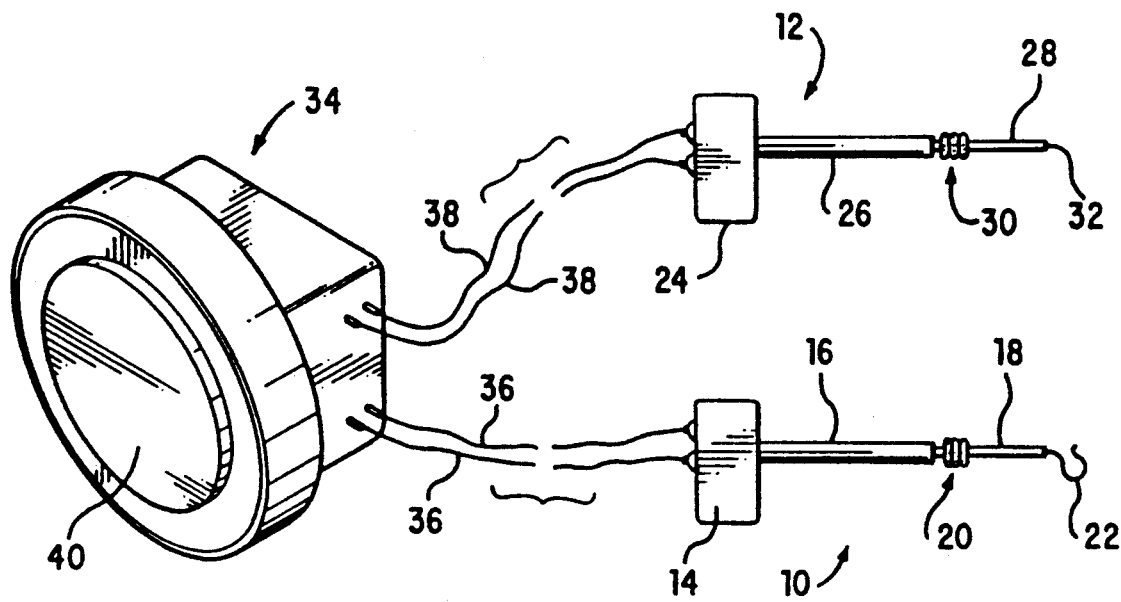
FIG. 3 is a detailed perspective view of the present invention.

The present invention provides a hermetically sealed transducer which may be used for both sound pick-up and sound delivery systems. In order to illustrate both of these uses, FIG. 3 illustrates the present invention providing both sound pick-up and sound delivery systems. Referring to FIG. 3, a sound pick-up mechanism 10 and a sound delivery mechanism 12 are illustrated.

The sound pick-up mechanism 10 includes an electromechanical transducer 14 (which acts as a microphone), an outer tube member 16, an inner tube or rod member 18 which extends beyond the end of the outer tube member 16 and a connective means 20 for providing a hermetically sealed connection between the inner and outer tube members 18 & 16, respectively (discussed in more detail below). The outer end of tube or rod member 18 may be connected to a wire hook 22 either by welding or other attachment means. The hook 22 is shaped to attach to one of the ossicular bones within the ear and serves to physically couple movement of the ossicular chain to transducer 14. Alternatively, the outer end of inner tube or rod can be made to acoustically couple with the tympanic membrane or membrane of the outer ear cavity as discussed in more detail below.

The sound delivery mechanism 12 is very similar in overall configuration to the sound pick-up mechanism 10. The sound delivery mechanism 12 includes an electromechanical transducer 24 (which acts as a transmitter), an outer tube member 26, an inner tube or rod member 28 which extends beyond the end of the outer tube member 26, and a connective means 30 for providing a hermetically sealed connection between the inner and outer tube members 28 and 26, respectively, as disclosed in more detail below. The outer end 32 of inner tube member 28 would then be affixed in any suitable manner to one of the existing inner ear bones to transmit the vibrations to the cochlea.

It is to be understood that the above-described means of attachment to the selected ossicular bones are presently preferred. However, there are alternate means for effecting acoustical coupling between the transducers and the ossicular member of interest. Where direct physical coupling to an inner ear bone is not required, sound pick-up mechanism 10 can be fashioned without wire hook 22. In this instance, the end of the inner tube member 18 is positioned within the middle ear either in contact with or behind the tympanic membrane of the ear so that movement of the tympanic membrane imparts a corresponding movement in inner tube or rod 18 by direct contact in the first case or by sound pressure variations in the entrapped air volume of the middle ear in the second case. In such an application, it may be necessary to give attention to placement of the sound pick-up mechanism 10 so that it does not lie on a standing wave null point within the middle ear cavity.

Figure 2:
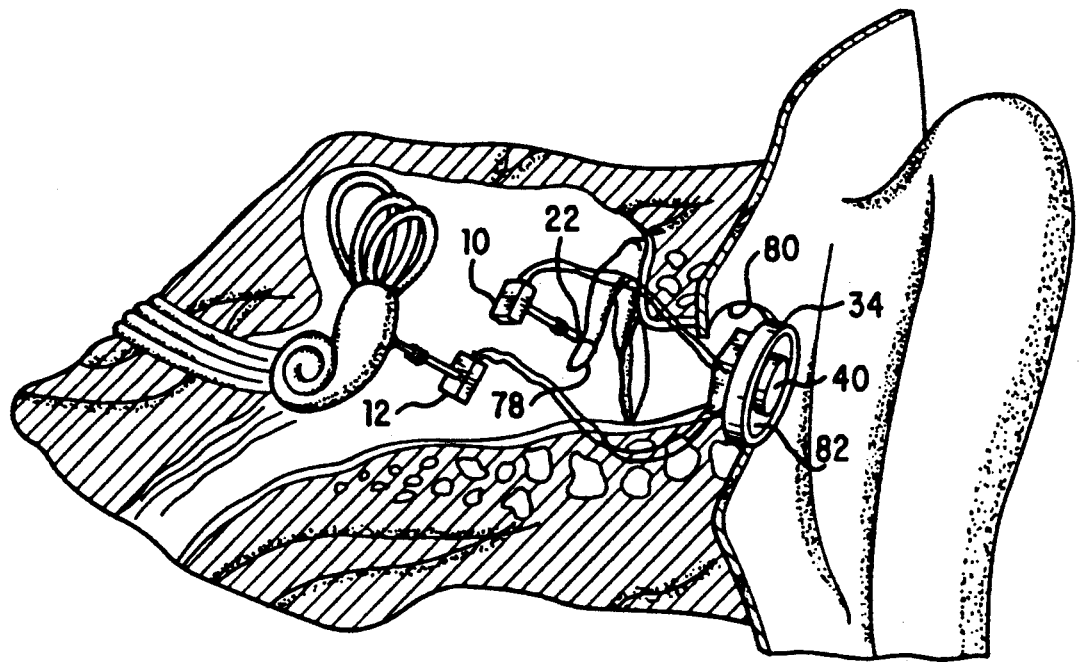
FIG. 2 is a posterior view of the human ear with one form of the invention implanted therein.
Figure 4:
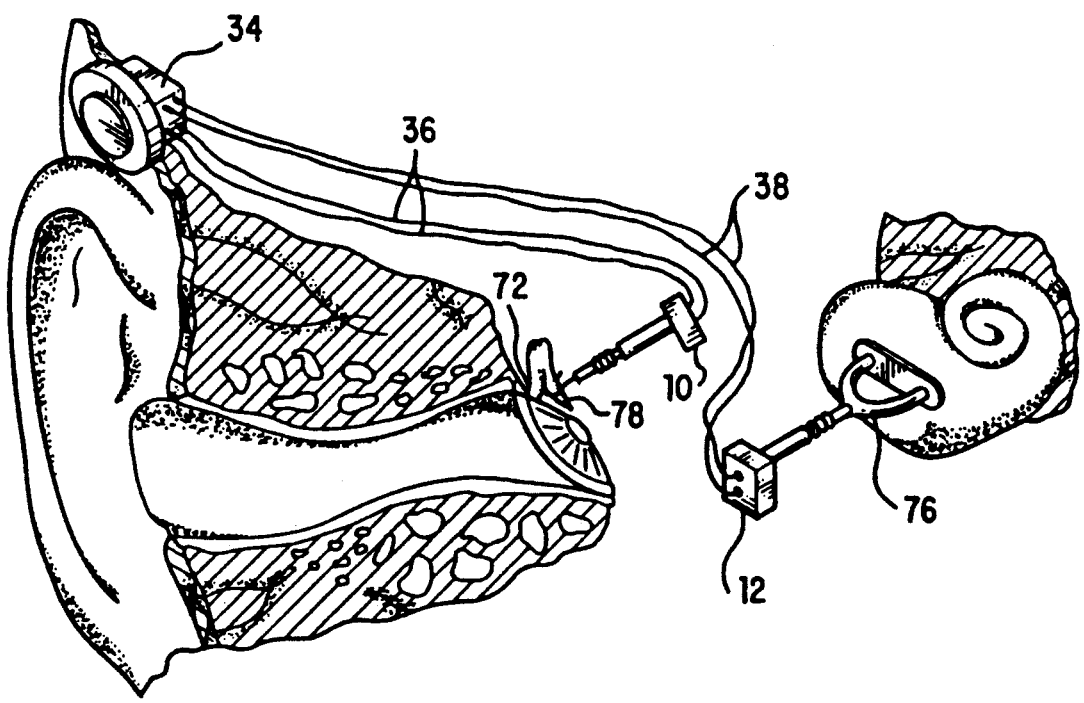
FIG. 4 is an enlarged perspective view of the human ear illustrating the invention shown in FIG. 3 in use.
Figure 7:
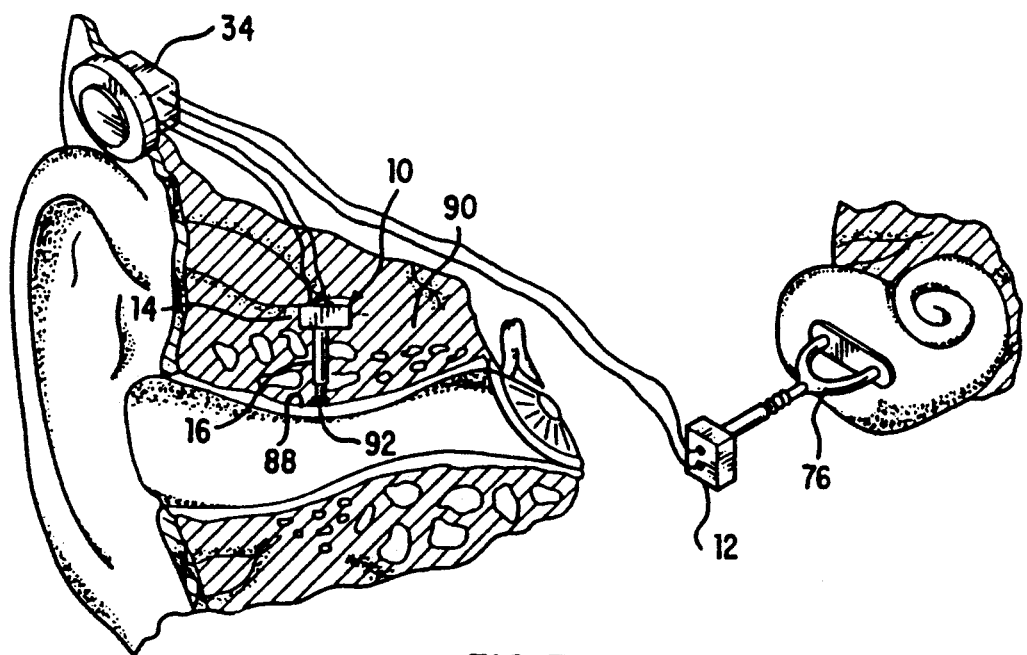
FIG. 7 is an anterior view of the human ear illustrating the invention implanted thereon in an alternate manner of use.

The electromechanical transducer 14 of the sound pick-up mechanism 10 and the electromechanical transducer 24 of the sound delivery mechanism 12 are both connected to a sound reinforcement and processing package 34 via two pairs of wires 36 and 38, respectively. The sound reinforcement and processing package 34 is preferably located outside the middle ear cavity as illustrated in FIGS. 2, 4 and 7. The package 34 typically would include amplification and signal processing electronic circuitry (not shown) to enable it to receive an electronic signal from the microphone/transducer 14 and transfer such signal in a readable fashion to the receiver/transducer 24 for transfer to the inner ear. To provide electrical power for operating the electronic circuitry, a battery 40 is secured to and electronically connected to the electronic circuitry within package 34. Preferably the battery 40 is rechargeable and the electronic circuitry includes an inductively coupled circuit means (not shown) for recharging the battery. In this regard, the circuit means would include an electromagnetic coil which would be positioned near the surface of the patient's skin and forms the secondary windings of a transformer. When it is desired to recharge battery 40, an external coil (not shown) is placed on or near the skin adjacent to the electromagnetic coil of the circuit means and forms the primary windings of a transformer. The primary and secondary coils are electromagnetically coupled with one another to form a transformer through which electrical energy is conveyed to charge battery 40.

Figure 5:
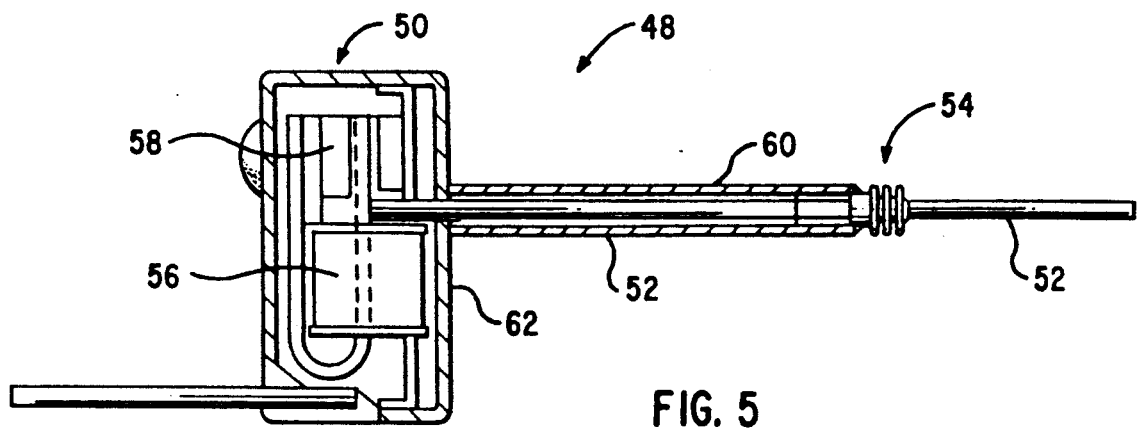
FIG. 5 is a cross-sectional view of the preferred embodiment of the present invention.
Figure 6:
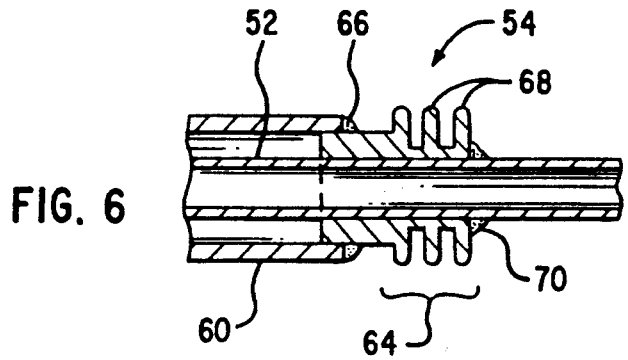
FIG. 6 is an enlarged cross-sectional view of the hermetically sealing bellows member of the connection means of the present the invention shown in FIG. 5.

To more fully describe the design of the sound pick-up mechanism 10 and the sound delivery mechanism 12 of FIG. 3, please refer to FIGS. 5 and 6 wherein one such mechanism 48, enlarged greatly and in partial cross-section is shown. The basic designs of sound pick-up mechanism 10 and sound delivery mechanism 12 are the same so for illustrative purposes only one such mechanism will be described here. The differences in the sound pick-up and delivery mechanisms relate to the manner in which the tips are connected into the ossicular chain (i.e. hook 22 or rod 28 as discussed above) and whether the mechanism is acting as a microphone or receiver. The detailed manner in which an electromechanical transducer operates will not be discussed here and for a more detailed understanding of the operation of such a transducer, please refer to U.S. Pat. No. 4,988,333 and U.S. application Ser. No. 420,292, filed on Oct. 12, 1989 which have been incorporated by reference herein.

The transducer referred to herein, whether acting as a sound pickup (microphone) or sound delivery (receiver) mechanism, utilizes the same connective means 54 to provide the proper hermetic seal for such transducers as described in the following paragraphs.

Referring to FIG. 5, the preferred embodiment of the transducer (used as either a microphone or receiver), is illustrated. An electromechanical transducer 50 is shown having an outwardly extending inner rod member 52 which acts in a piston-like manner to transmit physical movement in response to an electrical signal received by the transducer 50. The transducer 50 is of the type typically having a coil 56 and an armature 58 which is movable in response to a changing magnetic flux within the coil 56. An outer tube member 60 is attached to the transducer outer case 62 of transducer 50 to provide support and protection to inner rod member 52. The connective means 54 is provided at the outer junction of inner rod member 52 and outer tube member 60 and provides a hermetic seal therebetween.

Referring specifically to FIG. 6, the connective means 54 is shown in greater detail. The connective means 54 includes an accordion shaped bellows member 64. The bellows member 64 is affixed to the outer tube member 60 in an appropriate manner such as by providing a continuous weld 66 around the periphery of the bellows member and outer tube member end. The bellows member 64 is provided with a plurality of "U" shaped grooves 68 to give the side wall of the cylindrical bellows member a corrugated configuration. The material of the bellows member is either gold plated nickel or other biocompatible metal having sufficient strength and flexibility to provide a hermetic seal while still being flexible enough to allow axial movement of the inner rod member 52. As shown in FIG. 6, the inner rod 52 can be welded to the outer end of the bellows member 64 as shown at 70. Furthermore, hook 22 as shown in FIG. 3 or any other sound transmitting or receiving member may be added as is desired to provide the necessary coupling between the transducer and the human ear.

Strictly by way of example, the bellows member 64 may have an outside diameter (OD) of approximately 0.7 mm and an inside diameter (ID) of 0.4 mm and have a wall thickness of approximately 0.012 to 0.015 mm. It is desirable that the spring rate of the corrugated bellows should be less than the respective spring rates of all other components of the transducer 50 or the ossicles of the middle ear.

In another embodiment, it may be desirable to use a flexible hollow tube member in place of the inner tube member 52. The hollow tube member would have at least one end sealed to maintain a hermetically sealed transducer. The hollow tube member would be attached to the armature 58 and bellows member 64 in the same manner as inner rod member 52.

Figure 1:
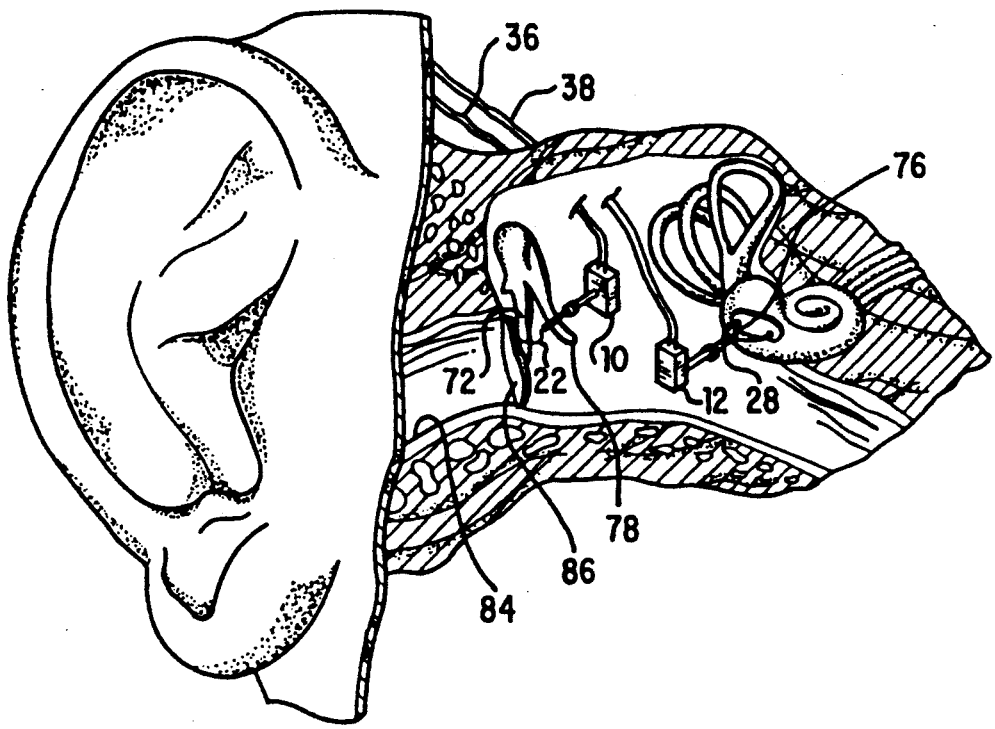
FIG. 1 is an anterior view of the human ear with one form of the invention implanted therein.

FIG. 1 illustrates one use of the invention wherein sound pick-up mechanism 10 is positioned within the middle ear cavity. The manner of attaching the sound pick-up mechanism 10 and sound delivery mechanism 12 within the ear cavity is not shown, however, it is envisioned that such mechanisms will be supported by fixation rods or otherwise secured in the patients bone and cartilage which surrounds the ear cavity. The sound pick-up mechanism 10 is attached by means of hook 22 to the malleus 72. The sound delivery mechanism 12 is also shown positioned within the cavity. The sound delivery mechanism 12 is attached to the auditory system by means of rigid rod 28 which contacts the head of the stapes 76. As illustrated, the ossicular chain is disarticulated by disconnecting two of the ossicular bones, such as at the incudostapedeal joint. In some cases, it may be necessary to remove the incus 78 to provide space and so as not to interfere with movement of the stapes now under control of sound delivery mechanism 12. The sound pick-up and delivery mechanisms may be installed by performing the appropriate surgical approach such as an atticotomy or mastoidectomy. The opening illustrated in FIG. 2 at 80 may then be used to receive the sound reinforcement and processing package 34, with either the secondary coil 82 or battery 40 being positioned immediately beneath the skin.

In use, the sound pick-up and delivery mechanisms as illustrated in FIGS. 1, 3 and 5 work as follows: Sounds enter the ear canal 84 and impinge upon the tympanic membrane 86, causing it to vibrate. The tympanic membrane, being attached to the malleus 72, thus imparts vibratory movement to the malleus. In a normal ear this movement of the malleus is transmitted through the incus 78 to the stapes 76. However, since the incus and stapes have been disarticulated, this movement is no longer communicated through the stapes. Instead, movement of the malleus acts through hook 22 to vibrate the inner rod member 18 of transducer 14 (see FIG. 3). Vibration of the inner rod member 18 transmits vibratory action to transducer armature 58 (FIG. 5). Coil 56 of transducer 14 converts the mechanical vibratory signal into electrical signals which are transmitted via wires 36 to the sound reinforcement and process package 34.

In many cases, the electrical signals will be amplified and may be additionally filtered to emphasize or de-emphasize various frequency ranges by the processing package 34 in accordance with the needs of the particular patient. Either analog or digital processing of the electrical signals can be employed. Using digital techniques, the electronic signal processing can be quite precise and quite frequency-selective, as needed. The objective of this signal processing is to provide a signal which compensates for deficiencies in the patient's hearing, in an effort to provide as much hearing as is possible.

After electronic amplification and signal processing, the electrical signal is fed through wires 38 to the sound delivery mechanism 12 which converts the electrical signals back into a vibratory mechanical signal via the coil 56 and armature 58 of transducer 24. These vibrations are then transmitted via inner rod member 28 to the middle ear bone (i.e. the stapes 72) of choice for transmission of the sound waves to the patient's cochlea.

FIGS. 2 and 4 illustrate another use of the invention wherein sound pick-up mechanism 10 is attached by means of hook 22 to the incus 78 instead of the malleus 72. Otherwise the sound pick-up and delivery mechanisms 10 and 12, respectively, operate to transmit sound to the stapes 76 in the same manner as specified above.

Referring now to FIG. 7, another use of the invention is illustrated wherein sound pick-up mechanism 10 is positioned so that the outer end 92 of inner rod member 18 abuts the ear canal as shown at 88. Sound pick-up mechanism is anchored within cartilage 90 to securely affix the mechanism in place. Sound waves entering the ear canal will cause the outer end 92 of rod member 18 of transducer 10 to vibrate thus transmitting such sound waves via inner rod member 18 through the outer intermediate tube member 16 to transducer 14 in the same manner as described above.

Another use of the invention allows the ossicular chain to remain intact by attaching the tip of 32 inner rod 28 of sound delivery mechanism 12 to either the malleus 72 or the incus 78 without removing any of the middle ear bones. This permits the hearing aid system of the present invention to act as a supplementary means in addition to the patient's residual hearing which is maintained by keeping the ossicular chain intact.

From the foregoing it will be seen that the present invention provides a solution to the problem of hermetically sealing an acoustic coupler or transducer for transmitting sound waves within the middle ear cavity. And, while the invention has been illustrated in an application utilizing both sound pick-up and sound delivery transducers, the invention may be adapted for other uses as well. For example, the sound delivery transducer may be adapted to transmit its signal directly into the cochlea. Alternatively, instead of utilizing an electromechanical transducer, the invention will use some other type of transducer or vibratory device capable of creating mechanical vibrations from auditory sound waves. Accordingly, it should be understood that the present invention is capable of certain modifications without departing from the spirit of the invention as set forth in the appended claims.

What is claimed is:

1. A hermetically sealed mechanism for an implantable hearing aid system, said mechanism comprising:
    a casing defining an interior space, said casing defining an aperture therethough;
    a movable member having a proximal end portion, an intermediate portion, and a distal end portion, said proximal end portion of said movable member being movably disposed within said interior space of said casing, said intermediate portion of said movable member being movably disposed through said aperture defined through said casing, and said distal end portion of said movable member being constructed to be coupled to a predetermined portion of human auditory system; and
    a bellows member having a first end portion, a second end portion, and a side wall, said side wall having a plurality of corrugations formed therein to permit longitudinal movement of said first end portion of said bellows member relative to said second end portion of said bellows member, said first end portion of said bellows member being hermetically sealed to said casing about said aperture defined therethrough and said second end portion of said bellows member being hermetically sealed to said movable member at a point external of said casing, whereby said bellows member surrounds a segment of said movable member, whereby said bellows member hermetically seals said interior space of said casing and said segment of said movable member from an ambient of said casing; whereby said distal end portion of said movable member is external of said casing and said bellows member, and whereby vibrational energy imparted to one end portion of said movable member is also imparted to an opposite end portion of said movable member.

2. A hermetically sealed mechanism in accordance with claim 1, wherein said casing comprises a casing body and an outwardly extending outer tube member having a proximal end portion mounted to said casing body about said aperture defined through said casing, said outer tube member having a distal end portion hermetically affixed to said first end portion of said bellows member, and wherein said movable member is axially mounted through said outer tube member.

3. A hermetically sealed mechanism in accordance with claim 1, wherein said bellows member is constructed of a biocompatible metal material.

4. A hermetically sealed mechanism in accordance with claim 3, wherein said bellows member is constructed of gold plated nickel.

5. A hermetically sealed mechanism in accordance with claim 1, said mechanism further comprising a transducer disposed within said interior space of said casing, said transducer being coupled to said proximal end portion of said movable member.

6. A hermetically sealed mechanism in accordance with claim 1, wherein said distal end portion of said movable member is constructed to be coupled to an ossicular bone of said human auditory system.

7. A hermetically sealed mechanism in accordance with claim 1, wherein said distal end portion of said movable member is constructed to be coupled to a tympanic membrane of said human auditory system.

8. A hermetically sealed mechanism for an implantable hearing aid system, said mechanism comprising:
    a first casing defining an interior space, said first casing defining an aperture therethrough;
    a first transducer disposed within said interior space defined by said first casing, said first transducer having capacity to generate an electrical output signal responsive to a vibrational input signal;
    a first movable member having a proximal end portion, an intermediate portion, and a distal end portion, said proximal end portion of said first movable member being disposed within said interior space of said first casing and being coupled to said first transducer, said intermediate portion of said first movable member being movably disposed through said aperture defined through said first casing, and said distal end portion of said first movable member being constructed to be coupled to a tympanic membrane of a human auditory system;
    a first bellows member having a first end portion, a second end portion, and a side wall, said side wall of said first bellows member having a plurality of corrugations formed therein to permit longitudinal movement of said first end portion of said first bellows member relative to said second end portion of said first bellows member, said first end portion of said first bellows member being hermetically sealed to said first casing about said aperture defined therethrough and said second end portion of said first bellows member being hermetically sealed to said first movable member at a point external of said first casing, whereby said first bellows member surrounds a segment of said first movable member, whereby said first bellows member hermetically seals said interior space of said first casing and said segment of said first movable member from an ambient of said first casing, whereby said distal end portion of said first movable member is external said first casing and said bellows member, and wherein vibrational energy imparted by said tympanic membrane to said distal end portion of said first movable member is imparted to said proximal end portion of said first movable member and to said first transducer;
    a second casing defining an interior space, said second casing defining an aperture therethrough;
    a second transducer disposed within said interior space defined by said second casing, said second transducer having a capacity to generate a vibrational output signal responsive to an electrical input signal;
    a second movable member having a proximal end portion, an intermediate portion, and a distal end portion, said proximal end portion of said second movable member being disposed within said interior space of said second casing and being coupled to said second transducer, said intermediate portion of said second movable member being movably disposed through said aperture defined through said second casing, and said distal end portion of said second movable member being constructed to be coupled to an ossicular bone of a human auditory system;

a second bellows member having a first end portion, a second end portion, and a side wall, said side wall of second bellows member having a plurality of corrugations formed therein to permit longitudinal movement of said first end portion of said second bellows member relative to said second end portion of said second bellows member, said first end portion of said second bellows member being hermetically sealed to said second casing, and said second end portion of said second bellows member being hermetically sealed to said second movable member at a point external of said second casing, whereby said second bellows member surrounds a segment of said second movable member, whereby said second bellows member hermetically seals said interior of said second casing and said segment of said second movable member from an ambient of said second casing, whereby said distal end portion of said second movable member is external said second casing, and whereby vibrational energy imparted by second transducer on said proximal end portion of said second movable member is imparted to said distal end portion of said second movable member and to said ossicular bone; and an electrical signal transmitter having a first end electrically coupled to said first transducer and a second end electrically coupled to said second transducer, whereby said electrical output signal of said first transducer is transmitted to second transducer.

9. A hermetically sealed mechanism in accordance with claim 8, wherein said first bellows member and said second bellows member are constructed of a biocompatible metal material.

10. A hermetically sealed mechanism in accordance with claim 9, wherein said firs bellows member and said second bellows member are constructed of gold plated nickel.

11. A hermetically sealed mechanism in accordance with claim 8, wherein said first casing and said second casing comprise respective first and second casing bodies and respective first and second outwardly extending outer tube members, and first and second outwardly extending outer tube members having proximal end portions mounted to said respective first and second casing bodies about said apertures defined through said respective first and second casings, said first and second outwardly extending outer tube members having distal end portions hermetically affixed to said first end portions of said respective first bellows member and said second bellows member, and wherein said first movable member is axially mounted through said first outwardly extending outer tube member and said second movable member is axially mounted through said second outwardly extending outer tube member.

12. A hermetically sealed mechanism for an implantable hearing aid system, said mechanism comprising:

a casing defining an interior space, said casing defining an aperture therethrough;

a movable member having a proximal end portion, an intermediate portion, and a distal end portion, said proximal end portion of said movable member being disposed within said interior of said casing, said intermediate portion of said movable member being movably disposed through said aperture defined through said casing, and said distal end portion of said movable member being constructed to be coupled to a predetermined portion of a human auditory system;

a transducer disposed within said interior space defined by said casing, said transducer being coupled to said proximal end of said movable member; and a bellows member having a first end portion, a second end portion, and a side wall, said side wall of said bellows member having a plurality of corrugations formed therein to permit longitudinal movement of said first end portion of said bellows member relative to said second end portion of said bellows member, said first end portion of said bellows member being hermetically sealed to said casing about said aperture defined therethrough and said second end portion of said bellows member being hermetically sealed to said movable member at a point external of said casing, said bellows member being constructed of a biocompatible metal material, whereby said bellows member surrounds a segment of said movable member, whereby said bellows member hermetically seals said interior of said casing and said segment of said movable member from an ambient of said casing, whereby said distal end portion of said movable member is external of said casing and said bellows member, and whereby vibrational energy imparted to one end portion of said movable member is also imparted to an opposite end portion of said movable member.

13. A hermetically sealed mechanism in accordance with claim 12, wherein said distal end portion of said movable member is constructed to be coupled to a tympanic membrane of a human auditory system, and wherein said transducer has a capacity to generate an electrical output signal responsive to a vibrational input signal.

14. A hermetically sealed mechanism in accordance with claim 12, wherein said distal end of said movable member is constructed to be coupled to an ossicular bone of a human auditory system, and wherein said transducer has a capacity to generate a vibrational output signal responsive to an electrical input signal.

* * * * *